United States Patent [19]

Mathiasmeier et al.

[11] Patent Number: 5,729,905
[45] Date of Patent: Mar. 24, 1998

[54] FOOT MEASURING APPARATUS AND CIRCUITRY TO ELIMINATE MULTIPLEXES AND DEMULTIPLEXERS

[75] Inventors: Michael Leo Mathiasmeier; William Eugene Fullen, both of Houston, Tex.

[73] Assignee: Dwayne L. Mason, Houston, Tex.

[21] Appl. No.: 526,669

[22] Filed: Sep. 11, 1995

[51] Int. Cl.[6] .................................................. A61B 5/103
[52] U.S. Cl. .................................................. 33/3 R
[58] Field of Search .......................... 33/511, 512, 3 R, 33/3 A, 3 B, 3 C; 128/779

[56] References Cited

U.S. PATENT DOCUMENTS

| | | | |
|---|---|---|---|
| 2,216,533 | 10/1940 | Kaplan | 33/3 C |
| 3,328,882 | 7/1967 | Blivice | 033/3 |
| 3,457,647 | 7/1969 | Cohen et al. | 33/3 R |
| 4,294,014 | 10/1981 | Baumann et al. | 33/3 C |
| 5,123,169 | 6/1992 | White et al. | 33/3 R |
| 5,128,880 | 7/1992 | White | 33/512 |
| 5,323,650 | 6/1994 | Fullen et al. | 128/779 |
| 5,361,133 | 11/1994 | Brown et al. | 33/515 |

FOREIGN PATENT DOCUMENTS

| | | | |
|---|---|---|---|
| 284922 | 10/1988 | European Pat. Off. | 33/512 |
| 285989 | 10/1988 | European Pat. Off. | 33/3 R |

*Primary Examiner*—G. Bradley Bennett
*Attorney, Agent, or Firm*—Dwayne L. Mason

[57] ABSTRACT

The invention pertains to an apparatus for measuring a foot's length and width to correspond to a shoe size and a method to eliminate multiplexers and demultiplexers in circuits. The apparatus is a low profile self-contained apparatus comprising a transducing medium, a microcontroller, a reference impedance element, a signal amplifier, an analog to digital conversion circuit, and a display to generate and display foot sizing data. A microcontroller unit [is connected directly to the hybrid multiplexing circuit which] contains algorithms which solve a set of linear equations to indirectly determine the electronic image of a foot. The shoe size is then calculated using a sizing algorithm and then displayed on a display which is connected to the output of the microcontroller unit.

24 Claims, 5 Drawing Sheets

FOOT MEASURING APPARATUS AND CIRCUITRY TO ELIMINATE MULTIPLEXES AND DEMULTIPLEXERS

BACKGROUND OF THE INVENTION

1. Field of the Invention

This invention relates to an apparatus used to measure and size human feet as a guide to fitting mass produced footwear. More specifically, it applies to electronic, solid-state designs intended primarily for self-service retail applications. This invention relates further to a method and circuit to eliminate multiplexers and demultiplexers in circuits.

2. Prior Art

With the inception of mass produced footwear, it was recognized that an efficient means by which to match the individual foot to the closest available standard last was required to simplify selection and insure proper fit. This resulted in the manufacture and patenting of a wide variety of devices ranging from simple metering sticks to assorted electronic, mechanical, electromechanical designs and even highly complex three-dimensional imaging systems. Such methods are well documented as cited in U.S. Pat. Nos. 4,294,014 5,323,650 and 5,123,169.

However, before evaluating such designs, a brief comment regarding the purpose and practicality of such a mechanism may help clarify the ensuing analysis. It should be noted that shoe sizing is not an exact science, primarily for two reasons. First, it is highly subjective in nature leading various manufacturers to place emphasis on different anatomical measurements such as ball girth, instep, waist and length in the last development. This is most evident by the fact that, while US manufacturers have more than ten designations governing width, European makers use length only. Second, although numerous sizing scales have been developed, no industry standard yet exists. Due to traditional practice and the competitive nature of last development and protection, most manufacturers continue to use their own sizing scales. This has resulted in the development of sizing methods with inconsistencies which prevent the development of a universal standard or even a consistent set of conversion factors long sought by international footwear distributors. What this means to the individual is that any 'size' provided by such a measuring device can be best interpreted as only a rough estimate or starting point to selection of mass produced footwear of varying manufacturer and local.

Regardless of the method used, in order to detect the pattern presented by a foot, some form of transducing medium is required. This is generally handled in one of two ways: (1) using one or more radiating transducers/transceivers which move physically across the sensing surface under control of synchronized servos or motors as realized in designs of U.S. Pat. No. 3,328,882 or using an array of numerous discrete stationary elements distributed the sensing plane as is realized in U.S. Pat. Nos. 4,294,014 and 5,323,650.

The first has the advantages of using a minimal number of transducers and associated control circuitry and theoretically infinite resolution. The disadvantages are the use of mechanical or electromechanical components which generally consume more power, are bulkier, less reliable and relatively more difficult to operate. The second has the advantages of simplified operation, compact design and enhanced reliability afforded by solid-state construction and disadvantages including a greater part count, use of discrete transducer elements, more complex control circuitry, finite resolution and more sophisticated manufacturing techniques.

The invention presented here is superior to previous designs because of its enhanced practicality achieved by taking advantage of the solid-state construction afforded by electronic designs, while avoiding the use of expensive discrete transducing elements and associated analog multiplexing (MUX/DEMUX) circuitry. This is achieved using a distributed transducer medium, rather than discrete transducers, wherein the transducer medium determines transducer values indirectly as the solution of a set of linear equations calculated in a microcontroller unit (MCU). Although this requires more sophisticated software, one skilled in the art will understand that this simply results in greater utilization of resources already inherent within the MCU.

SUMMARY OF THE INVENTION

In order to better understand the design details presented for this invention, a brief description of the operation is provided. Reference to conventional designs are also included, where instructive.

It will be instructive to first discuss the transducing medium used to convert the foot pattern to electrical signals processed by the MCU. The transducing medium includes a sensor array comprising a series of separately addressed conductive element pairs, which are distributed horizontally across a circuit board to form a sensing plane of thin contiguously placed strips. Each element impedance is a linear function of the total area between itself and the portion of a foot covering it. Thus, a transducing surface is produced which provides the outline or image of a foot placed on its surface by compiling a individual foot width measured at discrete intervals. The resolution being a function of the impedance measurement and element density. The advantage of such a configuration is that the distributed nature of the transducer medium avoids the use of discrete items such as LEDs, phototransistors, etc. such as that used in U.S. Pat. Nos. 4,294,014 and 5,323,650, and reduces the number of transducers in direct proportion to the horizontal resolution. The present inventions use is simplified since the user is free to place a foot anywhere within the sensor area.

The second part of the transducing medium includes an addressing circuit. The addressing circuit comprises a series of connections between the sensor array and the MCU, which allows the sensing plane to be divided discretely in the vertical direction using the separately addressed conductive element pairs and continuously in the horizontal direction by measuring in an analog fashion to obtain the width of a foot. This configuration is superior to existing designs because it reduces circuitry by eliminating the need for analog demultiplexers (DEMUXs), and allows the conductive elements to be connected directly to the MCU digital drivers. Thus, it takes advantage of the solid-state construction of a fully discrete design, while reducing the number of transducers by a factor proportional to the horizontal resolution. Further, the discrete or digital portion also makes use by reducing the number of addressing lines by a factor of $n^{(1/2)}/2$, where n is the number of conductive elements.

The final portion of the transducing medium is the addressor. Since the foot pattern covers a number of conductive element pairs, the present invention is capable of sensing the condition of all element pairs when one, two or all are activated simultaneously. The standard prior art systems which use a scanning MUX/DEMUX configuration to successively isolate each element are not used here because activating two or more element pairs at a time causes unwanted bridging capable of producing false readings. One solution to this problem was successfully handled by Baumann U.S. Pat. No. 4,294,014 using time or frequency division, which required multiplexed nonobstructive radiating transducers.

The present invention eliminates the need for both nonobstructive transducers and analog switching circuitry by connecting the sensor array directly to the MCU and utilizing the addressing circuit and addressor. Since the direct connections remove the ability to electrically isolate individual conductive element pairs, their values are determined instead by examining the entire sensor array under a number of different electrical configurations produced by the MCU I/O levels, and then deducing their values indirectly as the solution of a set of linear equations calculated by the MCU. The addressor comprises software routines in the MCU, which solve the linear equations and generate the electrical signals, which drive the sensor array. The addressor employs basic axioms of linear algebra, to a number of linearly independent electrical configurations equal to the number of conductive element pairs to solved for the width and length of the object being scanned.

One who is skilled in the art will appreciate that an infinite number of possible configurations for the present invention exist without departing from the scope of the present invention. For example, in an alternative embodiment, the sensor array comprises a continuous solid conductive material, which is connected directly to the MCU. However the components described above for the preferred embodiment are desired because the result is the low cost/low component design of the present invention, which was heretofore unachievable by prior art designs As with conventional multiplexing, n row and column drivers are used to address $n^2$ elements, except that in the present invention the n elements are tied directly together, sharing a common output. In the present invention all driver ground references first pass through a reference impedance element used as the reference for assessing the electrical status of the sensor array. The value of the reference impedance element is made small enough compared to the transducer medium and driver output impedance's so as to be nearly at ground level to ensure proper driver bias.

The $n^2$ linearly independent electrical configurations are obtained by scanning the array in a manner analogous to that of conventional multiplexing circuits. Each row driver is successively driven high with the others low, while one column driver remains high and the others low. Then the row drivers are scanned again with the previous column returned low and next made high. This is then repeated for all remaining combinations with the steady-state voltage, Vo, measured, converted to digital form and stored in the MCU RAM for use in later calculations. For each combination, current flows through all but n element pairs, one of which has a high logic 1 potential at both terminals and n−1 others having Vo potential at both terminals. Thus, summing the voltage drops for all combinations gives the following set of equations:

$$0*a1 + a2*dVo1 + a2*dVo1 + \ldots + an*dVo1 = GVo1$$
$$a1*dVo2 + 0*a2 + a2*dVo2 + \ldots + an*dVo2 = GVo2$$
$$a1*dVo3 + a2*dVO3 + 0*a2 + \ldots + an*dVo3 = GVo3$$
.
$$a1*DVon^2 + a2*dVOn^2 + a2*dVon^2 + \ldots + 0*an = GVo1$$

Where Voi is the reference voltage measured across R for the ith drive configuration, dVoi=V−Voi where V is the high logic 1 voltage potential, ai is the admittance of the ith transducer element and G is 1/R. Then dividing both sides by dVoi and expressing in matrix form gives:

$$B*a=V$$

where $$B = \begin{vmatrix} A11\ldots 1 \\ 1A1\ldots 1 \\ 11A\ldots 1 \\ . \\ . \\ . \\ 111\ldots A \end{vmatrix} \quad (n^2 \times n^2)$$

$$A = \begin{vmatrix} 0\,1\,1\ldots 1 \\ 1\,0\,1\ldots 1 \\ 1\,1\,0\ldots 1 \\ . \\ . \\ . \\ 1\,1\,1\ldots 0 \end{vmatrix} \quad (n \times n)$$

Where $a=[a1\ a2\ a3\ldots an^2]T$ is the transducer impedance vector and $V=[Vo1/dVo1\ldots Von^2/dVon^2]T$ is the vector of measured reference voltages.

Solving for "a" gives $$a=B*V$$

where $$B = \begin{vmatrix} P\,Q\,Q\ldots Q \\ Q\,P\,Q\ldots Q \\ Q\,Q\,P\ldots Q \\ . \\ . \\ . \\ Q\,Q\,Q\ldots P \end{vmatrix} \quad (n^2 \times n^2)$$

and $$P=[(n-2)*A-(n^2-5*n+5)*I]/2/(n-1)/(n-2)\ (n \times n)$$

$$Q=-[A-(n-2)*I]/2/(n-1)/(n-2)\ (n \times n)$$

Where the components of the resulting vector, a, are the $n^2$ values equal to the measured widths of each of the individual Conductive elements. The redundant, symmetrical nature of the inverse readily lends itself to numerical manipulation by the MCU. It should be noted that although an exact square number of elements are required theoretically to produce a nonsingular coefficient and, hence, a solution, any number of conductive elements may actually be used. The next highest exact square is simply chosen for calculation with all surplus admittance's set to zero.

Finally, although the system is theoretically valid, there exist parasitic impedance's in the actual hardware used in construction which impose practical limitations, which require slight model modifications to ensure proper function. These include the nonsymmetrical nature of the output drivers and extraneous impedance's resulting from the sensor array distribution.

First, although the driver outputs were depicted as simple single pole double through SPDT switches for simplicity, actual switching contains active complimentary drivers which exhibit different impedance's for high and low states. Incorporating these impedance's, labeled Gl and Gh, for low and high outputs, respectively, and assuming all impedance's of respective states are equal:

$$A*[Va-(Vo-Verr)]*G=(Vo-Verr)*Go$$

$$Go*(vo-Verr)=(V-Va)*Gh$$

$$a'=a/(1+a/Gl)$$

Where Va is the actual driver logic 1 output voltage and Verr is the deviation of the measured output from the ideal value, Vo. Note, Verr is always positive because the added impedance's always result in a smaller actual output voltage than the ideal value. Also, Gl may be grouped with "a", because although it is connected to n−1 other conductive elements, only "a" actually has current through it.

Next, eliminating Va and solving for Verr gives:

$$Verr=\{(A+go*l)T-\{(A+Go*l)T-[(1+go/gh)*A+Go*l]T\}*A*V$$

Noting that the Verr approaches 0 and a' approaches "a" as the ratios a/Gl and go/Gh decrease confirms the intuitive assumption that large values of transducer characteristic impedance's (>50 k ohm) must be used to minimize the effect of the drivers.

Though the second source of parasitic impedance, due to the leakage current between contiguous drive B outputs, may not exist in a dc drive system using conductive elements, it has significant influence in the preferred embodiment. It is mentioned here because of the modifications which must be made to the ideal model presented above. It can be shown that, for large enough transducer densities such that the widths measured by adjacent elements are roughly equal, the parasitic impedance's can be modeled by adding 1 to all values in column 1 and n of the group matrix, A', giving:

$$A' = \begin{vmatrix} 1 & 1 & 1 & \ldots & 2 \\ 2 & 0 & 1 & \ldots & 2 \\ 2 & 1 & 0 & \ldots & 2 \\ . & & & & \\ . & & & & \\ . & & & & \\ 2 & 1 & 1 & \ldots & 1 \end{vmatrix} \quad (n \times n)$$

Aside from a more practical circuit design, the proposed device also takes greater advantage of MCU resources to make the unit more flexible and easier to use. This is achieved in three ways: (1) by storing a number of different standard sizing scales internally within the MCU ROM for enhanced versatility, (2) using the computational abilities of the MCU to provide additional fitting information and (3) use of a series of hardware interrupt routines to fully automate device operation.

Finally, hardware interrupts and a series of associated routines are employed to fully automate and simplify operation such that no user input is required. This also simplifies manufacturing and enhances reliability by eliminating the need for buttons, switches or other mechanical adjustments. This includes MCU wakeup and sleep modes which help conserve power by monitoring use and automatically shutting off the display and all other nonessential circuit activity upon detecting a time out idle state. Also, option selection is further simplified by automated selection routines which use the display and sensor pad to prompt the user for input. If no user input is detected after prompting, the unit than automatically activates the most commonly used option as default. In the preferred embodiment, this includes the option of selecting among various established sizing systems including Mondopont, German Stich as well as the various subscales for gender and age upon power-up which automatically defaults to the U.S. system if no selection is specified.

Aside from facilitating operation, such an autonomous, self-managing algorithm also improves reliability by employing exclusive use of linked, autonomous code blocks supported by the time-out redirection and default parameters mentioned above. This fully automates operation such that the user is allowed to select options, while at the same time never actually possessing control of device operation. The aforementioned safeguards, combined with the automated sleep/wake-up modes and internal watchdog routines all serve to improve reliability by insuring that the operation is relatively immune to faulty programming caused by ambiguous, invalid or unspecified input conditions, internal latch-ups, computation errors or improper control settings.

In summary, the present invention facilitates the sizing of mass produced footwear, while offering improved performance and efficiency over existing designs by using solid-state construction employing a distributed transducer medium connected directly to the MCU to reduce apparatus circuitry, reduce power consumption and provide a compact construction for portability. In addition, internal MCU routines are incorporated to enhance versatility and simplify use by automating operation, programming and option selection, while offering a selection of sizing scales and surplus sizing information.

The invention is described in detail on the basis of the following description, attached drawings and schematics.

DETAILED DESCRIPTION OF THE DRAWINGS

Figure 1:
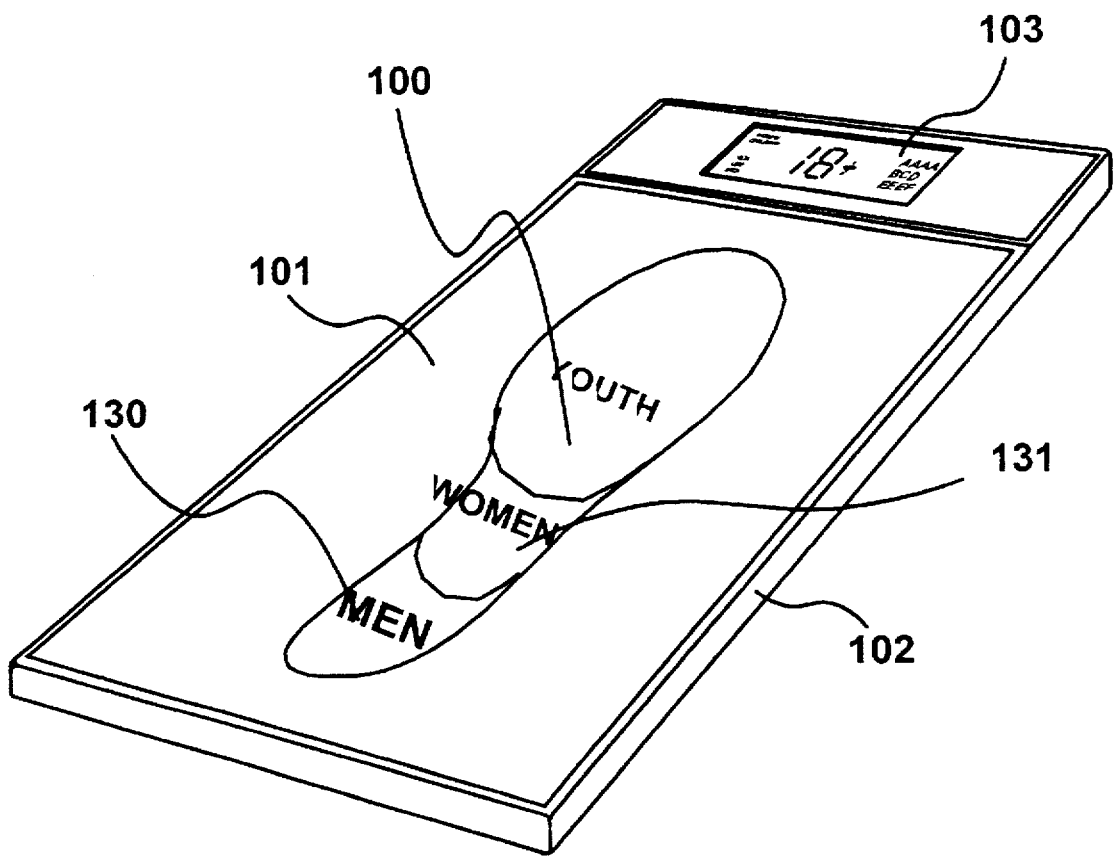
FIG. 1 is a general outline view of the apparatus.

As shown in FIG. 1, the preferred embodiment of the apparatus 100 includes a protective sensor pad 101 for placement of a foot, a liquid crystal display (LCD) 103 for displaying the corresponding sizing information, and a protective enclosure 102 for housing the respective parts.

Figure 2:
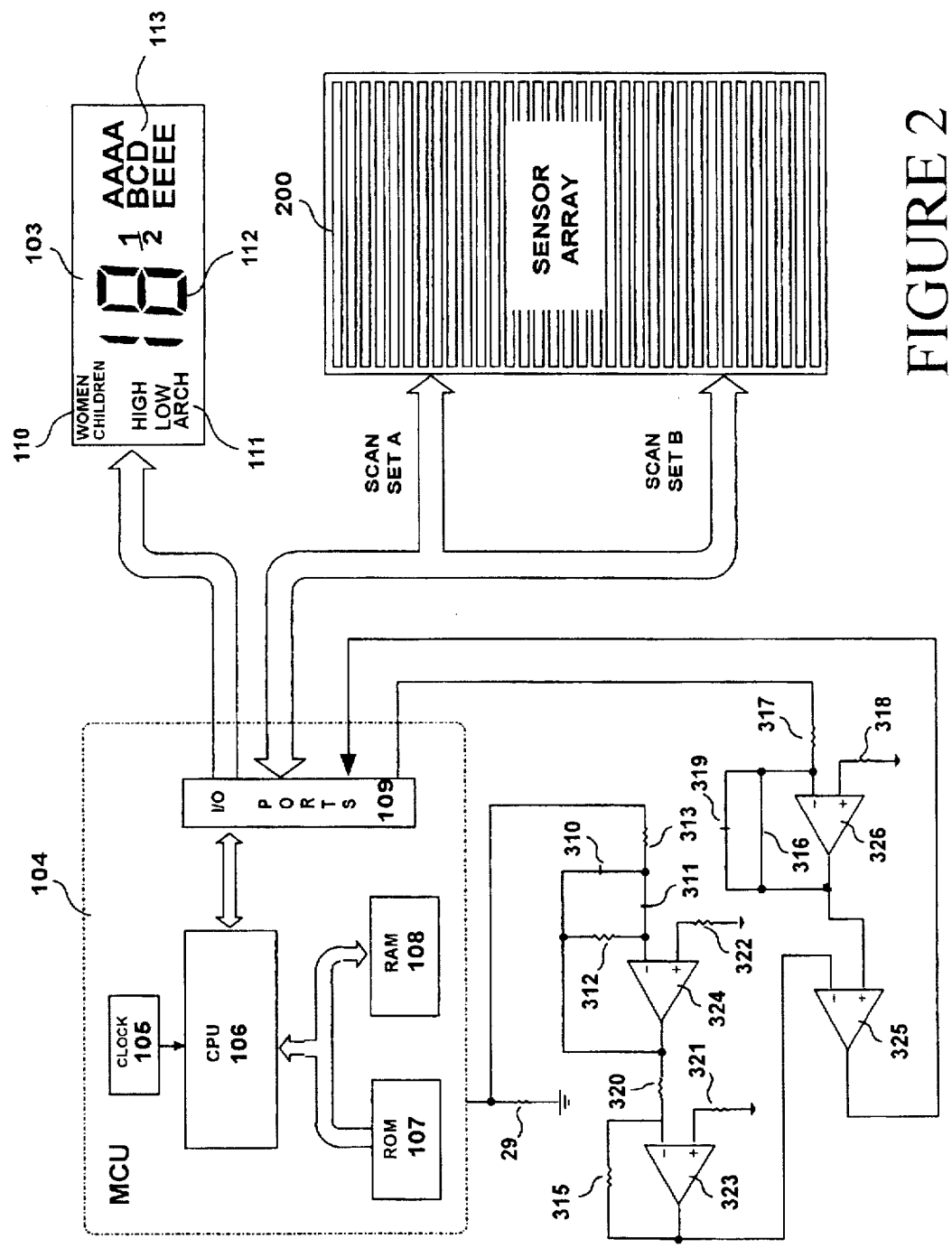
FIG. 2 is a block diagram of overall circuit schematic.

As shown in FIG. 2, the sensor array 200 contains a series of distributed transducers connected to the MCU I/O ports 109. Although either passive or reactive transducers may be used, the preferred design employs passive conductive elements driven by AC signals because it simplifies manufacturing, reduces cost, and enhances reliability by avoiding the tighter tolerances, conductive compounds, and coupling elements associated with the prior art discrete element designs. The passive conductive elements are driven by AC drive signals, which create the conditions required to mathematically solve for the foot image via an internal software routine in the MCU 104, which produces inverse phase square waves. This also serves to average out the nonsymmetrical nature of the high and low driver impedance's which may otherwise distort the result.

Figure 3:
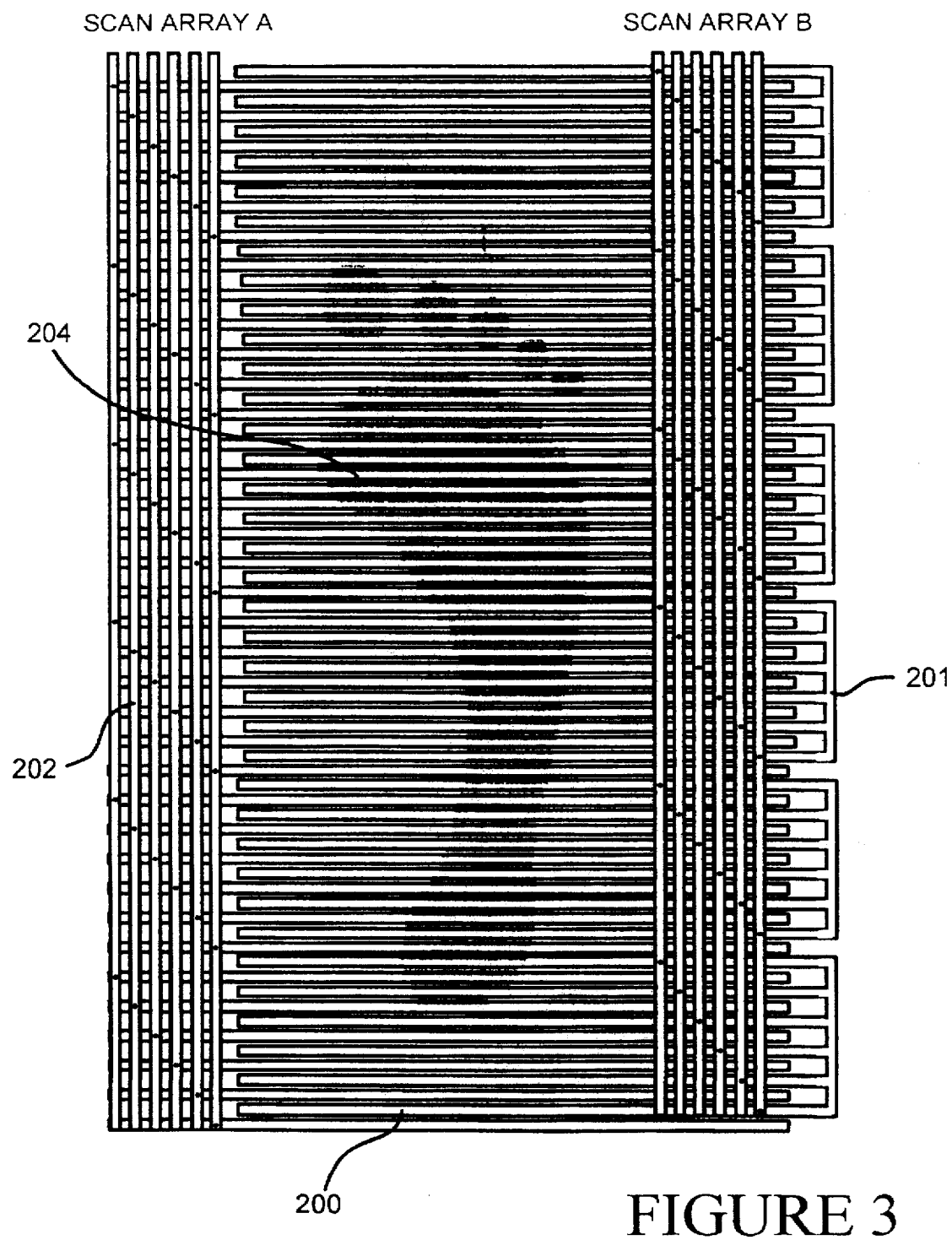
FIG. 3 is a schematic showing the sensor array and addressing circuit.

Referring now to FIG. 3, the sensor array 200 includes a plurality of horizontal conductive element pairs 201, which are connected to the MCU by a plurality of vertical traces 202, which comprises a portion of the addressing scheme and is arranged in a contiguous fashion across the sensing area. The sensor array 200 may be formed in various ways including silk screening conductive ink upon a mylar substrate or using a standard etched copper printed circuit board as utilized in the preferred embodiment. The etched copper printed circuit board (PCB) has the advantage of simplifying fabrication by allowing the sensor array 200 and the remaining circuitry to share the same PCB producing a single board unit in a single etching operation. The outline of a foot 204 (as shown on FIG. 3) having been placed on the sensor pad 101 is determined by detecting the change in impedance produced by the permitivity of the human foot where it lies in close proximity to the sensor array 200.

One who is skilled in the art will readily understand that impedance is directly proportional to the width of the region where the foot contacts the sensor pad 101. Therefore, by using a sensor array 200 comprising conductive element pairs 201 of equal width and spacing, the width of a foot at discrete intervals can be measured and compiled to generate an image of the outline of a foot 204. The image resolution being a function of the precision of the measurement and element pair density.

Figure 4:
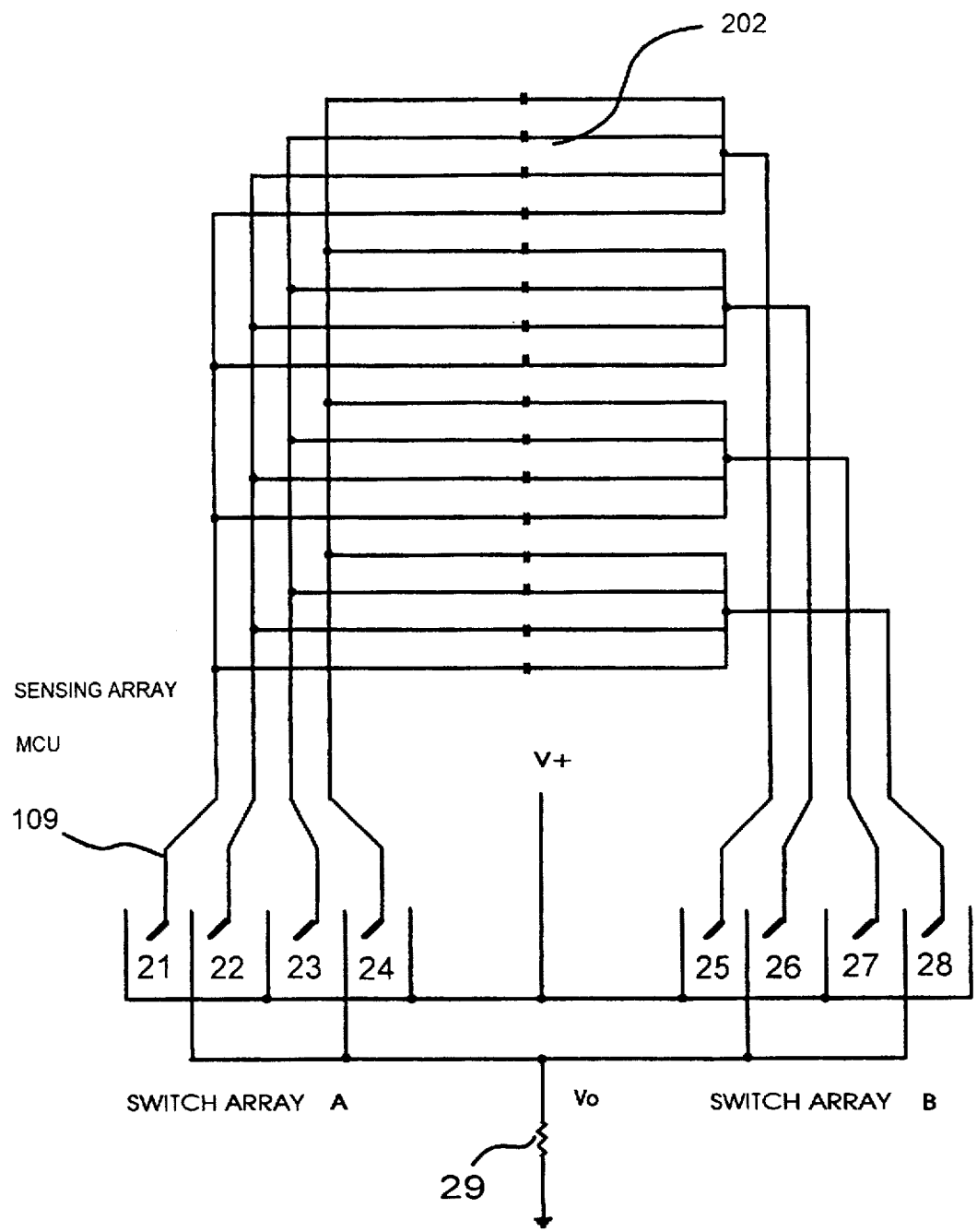
FIG. 4 is a schematic showing the addressing scheme circuitry.

The next component of the foot measuring apparatus 100 to be discussed, is the addressing scheme circuitry. The addressing scheme circuitry included the vertical traces 202, MCU i/o's 109, and the reference impedance element 29 shown in the simplified diagram of FIG. 4. The addressing circuitry divides the sensing plane discretely in the vertical direction, using switch array A 21 through 24 and switch array B 25 through 28 to address conductive element pairs 201, and continuously in the horizontal direction by measuring width indirectly in an analog fashion using the same conductive element pairs 201. As previously discussed, the ground references are shown passing through the reference impedance element, which in the preferred embodiment is a resistor 29 for assessing the electrical status of the individual conductive element pairs 201.

Though the addressing scheme circuitry described may be of any type having both high (supply) and low (ground) active outputs the preferred embodiment uses the I/O pins of the MCU 104 central processing unit (CPU) 106 directly to reduce circuitry components as distinguished from the prior art devices. This means the ground rail of the MCU 104 must be placed in series with the reference resistor 29, since the ground reference of all drivers are connected internally. This causes no problem as long as the maximum possible reference voltage, Vo, is maintained low enough (<100 mV) so as to not interfere with MCU operation. Also, the internal activity of the MCU, i.e., software routines, counters, etc. must be negligible, identical for each driving configuration or filtered as is done in the preferred embodiment using an analog active filter design shown in FIG. 2 as components 310, 311, 312, 313, 322, 323, 319, 320, 321, and 324 to remove such parasitic currents which would interfere with the sensor array current corrupting the measurement. As shown in FIG. 2, the preferred embodiment uses the Motorola MC68HC05C9 with 24 I/O pins for addressing 144 electrode pairs and a reference resistor 29 producing a maximum Vo of less than 100 mV.

It will be instructive now to discuss further the microcontroller 102 as shown in FIG. 2. The MCU 104 comprises a clock 105, the CPU 106, read only memory (ROM) 107, and random access memory (RAM) 108. Ideally, any device (s) providing basic arithmetic operations, data processing and storage will suffice, however in the preferred embodiment, a single chip VLSI microcontroller, providing all these functions on board, is preferred due to their relative economy, small package, minimal power consumption and availability. Specifically, the preferred embodiment employs the Motorola MC68HC05C9. This provides a generous 352 bytes of RAM, 15.9 KB of ROM, 31 I/O pins for driving up to 225 transducer elements and internal watchdog routines to improve reliability. Aside from providing all of the necessary computation and storage functions, the MCU 104 is also used to directly drive both the LCD 103 and sensor array 200 as well as the counting and pulse generating functions used with the external op amp integrator 315, 316, 317, 318 325 and comparator 326 to perform analog to digital (ND) conversion of the signal voltage across the reference resistor 29.

Since the scanning routine used to image the foot pattern takes only a fraction of a second, read/write routines can operate separately such that the LCD 103 and sensor pad 201 are not required to operate simultaneously. This provides the added benefit of further reducing circuitry by using the same MCU I/O pins 109 to control both. To achieve this, the LCD 103 backplane or common connection is placed in a high impedance state to disconnect it while the sensor array 200 is being read. All that is required is that the effective impedance of the sensor array 200 is small enough, approximately 200 times less than the parasitic impedance of the LCD 103, so that it does not interfere with display operation.

Figure 5:
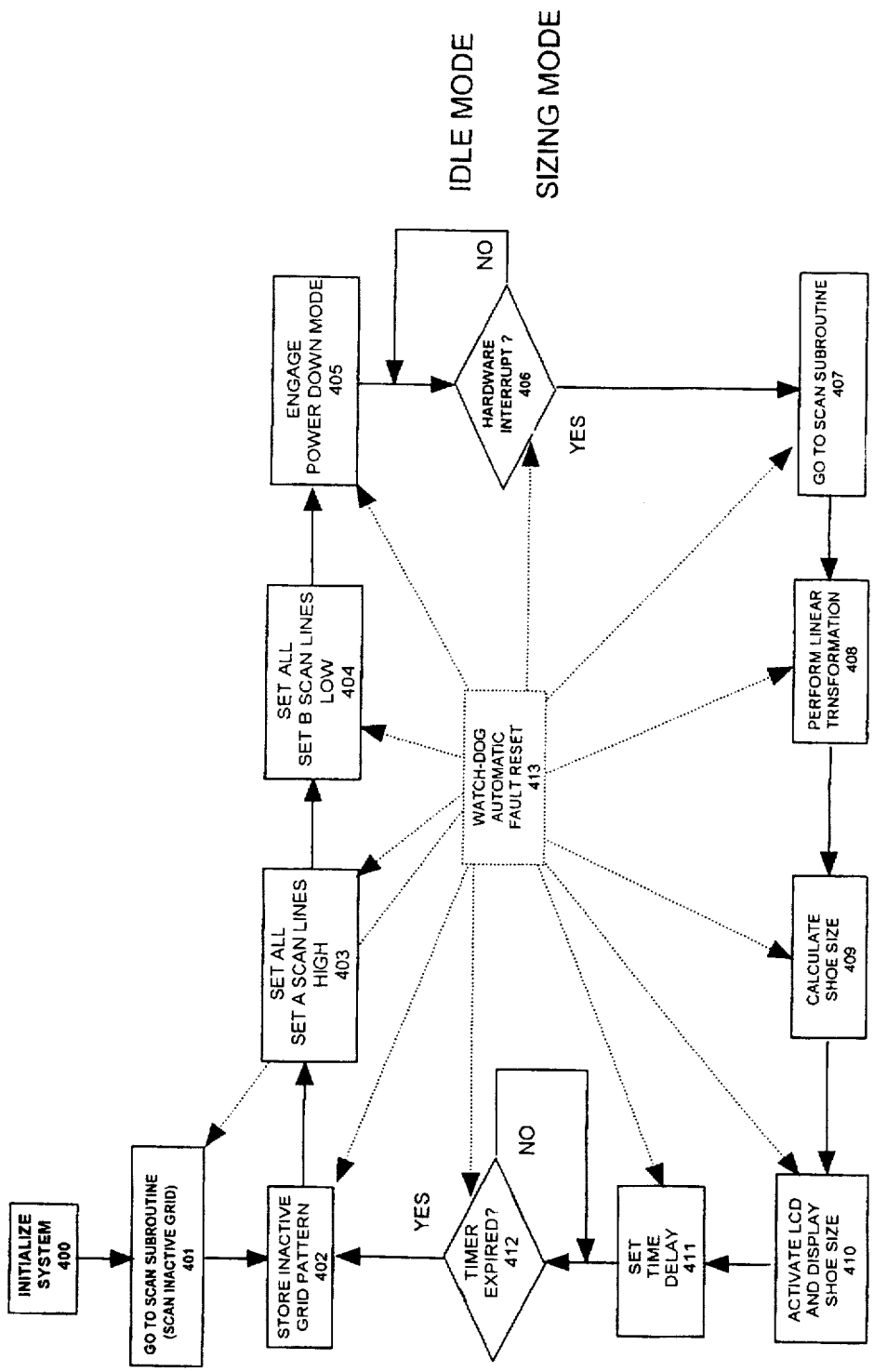
FIG. 5 is a flow diagram of the software and algorithms in the microcontroller.

Although the exact coding of the MCU program depends upon the specific MCU selected, a basic flow diagram used in construction of the preferred embodiment and generally applicable to most any MCU is shown in FIG. 5. Principle elements of the algorithm include the exclusive use of linked, autonomous code blocks supported by time-out redirection 406, 412 and default parameters. This fully automates operation such that the user is allowed to select options, while at the same time never actually possessing control of device operation. Thus, combined with the automated sleep/wake-up operation and internal watchdog routines 413, shown dashed in FIG. 5, this serves to both simplify operation and improve reliability by ensuring operation is relatively immune to faulty programming caused by ambiguous, invalid or unspecified input conditions, internal latch-ups, computation errors or improper control settings.

The program is divided into three primary modes of operation: (1) the power-up or initialization mode, (2) idle or sleep mode and (3) sizing mode. Upon power up, the apparatus first executes the initialization routine 400, which configures memory, register and I/O port settings and prompts the user to select the sizing scale desired. It then performs an initial sizing operation without a foot present to construct an electronic image of the sensor array 200 itself to identify and record sensor array 200 anomalies such as conductive element width variations, cracks and parasitic particles arising from non-ideal manufacturing processes, aging and normal wear and tear. This is then compared with actual sizing images during use to filter out such irregularities which may otherwise distort the measured image resulting in inaccurate sizing.

After initialization, the apparatus then enters the idle mode designed to reduce power consumption between sizing exercises. During this mode, the MCU 104 is placed in a sleep mode in which all internal operations except clock and memory retention are halted such that, combined with JFET op amp construction 323, 324, 325 and 326, minimal current consumption is achieved, which prolongs battery life.

To further facilitate operation, transfer between idle and active sizing modes is done automatically by continuously monitoring the sensor pad for activity. When no activity is sensed before expiration of a preset time delay 411, the MCU 102 then automatically returns to the idle mode, enables the external interrupt and places a static potential across the sensor array 403, 404 which allows the unit to remain in a static, low current state, until activated by the level transition at the external interrupt pin of the MCU, 406. This is caused by the transient charging current produced by the change in impedance resulting from the initial foot placement. This then initiates the interrupt, waking the MCU 102 and placing it in the active sizing mode. When brought out of the idle mode, the device automatically scans the sensing area for a foot image 407 through 410 and displays the corresponding size in accordance with the scale selected. Aside from the particular sizing system selected the device also can be made to automatically adjust to the proper sub-scale relating to gender and/or age without requiring adjustment by the user. This is achieved by dividing the sensor pad 101 into specific regions for men 130, women 131 and youth 132 as depicted in FIG. 1 and making absolute as well as relative measurements. Although foot size is determined with the foot placed anywhere within the sensor pad boundary by measuring the relative distance between heel and toe, automatic scale adjustment can be added by directing the user to place their heel in the appropriate region using labels 130, 131, 132 and display prompts 110 and measuring the absolute distance from the sensor array 200 edge. Thus, by detecting the proper scale placement, the apparatus is able to determine the proper scale automatically without user adjustment, thus providing optimum versatile, multipurpose operation, while still maintaining a simple and easy sizing procedure.

Those who are skilled in the art will readily perceive how to modify the present invention still further. Thus, many possible embodiments may be made of the present invention without departing from the scope thereof, it is to be understood that all matter herein set forth or shown in the accompanying drawings is to be interpreted as illustrative and not in a limiting sense. According the foregoing description should be regarded as only illustrative of the invention, whose full scope is measured by the following claims.

We claim:

1. An apparatus for measuring and analyzing a foot, said apparatus comprising:

a transducing medium to convert a foot pattern to electrical signals;

a microcontroller coupled to said transducing medium for applying electrical signals to said transducing medium and for processing said electrical signals to generate foot sizing data;

a reference impedance element coupled with said microcontroller for use by said microcontroller as a reference for assessing the electrical status of the transducing medium; and a display for displaying foot sizing data generated by the microcontroller.

2. The apparatus of claim 1, wherein said transducing medium comprises a sensor array, an addressing circuit coupled to said sensor array, and an addressor for addressing the sensor array for use in the microcontroller.

3. The apparatus of claim 2, wherein said sensor array comprises a plurality of conductive element pairs.

4. The apparatus of claim 2, wherein said addressor comprises:

a first software routine within said microcontroller for generating electrical signals applied to said sensor elements to obtain a set of measured voltage values across said reference impedance element;

a second software routine within said microcontroller for performing a linear transformation to indirectly solve for each sensor element voltage value using the set of measured voltage values across said reference impedance element resulting from said first software routine.

5. The apparatus of claim 1, wherein said microcontroller, reference impedance element, signal amplifier, analog to digital conversion circuit, and display are disposed on a circuit board.

6. The apparatus of claim 1, wherein said display is a liquid crystal display.

7. The apparatus of claim 1, wherein said reference impedance element comprises a reference resistor.

8. The apparatus of claim 7, wherein the voltage drop across said reference resistor is maintained low enough so as to not interfere with microcontroller operation.

9. The apparatus of claim 1, wherein the microcontroller is a single chip microcontroller comprising:

a central processing unit for executing instructions controlling said scanning circuitry and for processing said data indicative of foot size;

a clock coupled to said central processing unit for synchronizing microcontroller unit operations;

read only memory coupled to said central processing unit for storing routines, data, and subroutines of instruction to be executed by said central processing unit; and random access memory for storing measured data, transformed data, and calculated data of instructions to be executed by said central processing unit.

10. The apparatus of claim 1, wherein said display is connected in parallel with said sensor array, and wherein the impedance of said sensor array is less than the impedance of said display.

11. The apparatus of claim 1, further comprising:

a signal amplifier for amplifying electrical signals;

an analog to digital conversion circuit for converting electrical signals for use by the microcontroller;

a protective enclosure for housing and protecting the microcontroller, sensor array, reference impedance element, amplifier, analog to digital conversion circuit, and display; and, a sensor pad disposed within a upper portion of said protective enclosure for placement of a foot.

12. The apparatus of claim 1, wherein said microcontroller is battery powered.

13. An apparatus for measuring and analyzing a foot of a man, woman, or youth, said apparatus comprising:

a sensor array configured to receive and transmit a plurality of electrical signals;

a microcontroller coupled to said sensor array for applying electrical signals to and analyzing electrical signals from said sensor array to generate foot sizing data;

a reference impedance element coupled with said microcontroller for use by said microcontroller as the reference for assessing the electrical status of the transducing medium; and a display for displaying foot sizing data generated by the microcontroller.

14. The apparatus of claim 13, wherein said transducing medium comprises a sensor array, an addressing circuit coupled to said sensor array, and a addressor for addressing the sensor array for use in the microcontroller.

15. The apparatus of claim 14, wherein said sensor array comprise a plurality of conductive element pairs.

16. The apparatus of claim 14, wherein said addressor comprises:
   a first software routine within said microcontroller for generating electrical signals applied to said sensor elements to obtain a set of measured voltage values across said reference impedance element;
   a second software routine within said microcontroller for performing a linear transformation to indirectly solve for each sensor element voltage value using the set of measured voltage values across said reference impedance element resulting from said first software routine.

17. The apparatus of claim 13, wherein said transducing medium, microcontroller unit, impedance element, signal amplifier, analog to digital conversion circuit, and said display are disposed on a circuit board.

18. The apparatus of claim 13, wherein said display is a liquid crystal display.

19. The apparatus of claim 13, wherein said reference impedance element comprises a reference resistor.

20. The apparatus of claim 19, wherein the voltage drop across said reference resistor is maintained low enough so as to not interfere with microcontroller operation.

21. The apparatus of claim 13, wherein said display is connected in parallel with said sensor array, and wherein the impedance of said sensor array is less than the impedance of said display.

22. The apparatus of claim 13, further comprising:
   a signal amplifier for amplifying electrical signals;
   an analog to digital conversion circuit for converting electrical signals for use by the microcontroller;
   a protective enclosure for housing and protecting the microcontroller, sensor array, reference impedance element, amplifier, analog to digital conversion circuit, and display; and,
   a sensor pad disposed within a upper portion of said protective enclosure for placement of a foot.

23. The apparatus of claim 13, wherein said microcontroller comprises:
   a central processing unit for executing instructions controlling said scanning circuitry and for processing said data indicative of foot size;
   a clock coupled to said central processing unit for synchronizing microcontroller unit operations;
   read only memory coupled to said central processing unit for storing routines, data, and subroutines of instruction to be executed by said central processing unit; and
   random access memory for storing measured data, transformed data, and calculated data of instructions to be executed by said central processing unit.

24. The apparatus of claim 13, wherein said microcontroller is battery powered.

* * * * *